(12) United States Patent
Burger et al.

(10) Patent No.: US 7,695,281 B2
(45) Date of Patent: Apr. 13, 2010

(54) METHOD AND SYSTEM FOR DESIGNING A DENTAL REPLACEMENT

(75) Inventors: Bernd K. Burger, Alling (DE); Michael A. Kraemer, Landsberg (DE); Markus P. Salex, Martinsried (DE)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 10/987,492

(22) Filed: Nov. 12, 2004

(65) Prior Publication Data

US 2006/0105294 A1 May 18, 2006

(51) Int. Cl.
*A61C 11/00* (2006.01)
(52) U.S. Cl. .................................... 433/213
(58) Field of Classification Search ............. 433/167, 433/201.1, 213, 223; 700/182; 382/128, 382/154
See application file for complete search history.

(56) References Cited

U.S. PATENT DOCUMENTS

| 5,273,429 | A | * | 12/1993 | Rekow et al. ............ 433/215 |
| 5,382,164 | A | | 1/1995 | Stern |
| 6,261,098 | B1 | * | 7/2001 | Persson .................... 433/213 |
| 6,431,870 | B1 | * | 8/2002 | Sachdeva .................. 433/213 |
| 6,851,949 | B1 | * | 2/2005 | Sachdeva et al. .......... 433/213 |
| 6,970,760 | B2 | * | 11/2005 | Wolf et al. ................ 700/163 |
| 7,092,780 | B2 | * | 8/2006 | Ganley et al. ............. 700/117 |
| 2002/0028418 | A1 | * | 3/2002 | Farag et al. ............... 433/29 |
| 2004/0151367 | A1 | * | 8/2004 | Wolf et al. ................ 382/154 |
| 2004/0204787 | A1 | * | 10/2004 | Kopelman et al. ......... 700/182 |
| 2005/0089822 | A1 | * | 4/2005 | Geng ........................ 433/215 |
| 2006/0093987 | A1 | * | 5/2006 | Wen .......................... 433/74 |

FOREIGN PATENT DOCUMENTS

| EP | 0067880 A1 | 12/1981 |
| EP | 0490848 A2 | 11/1991 |
| WO | WO 97/21156 | 6/1997 |
| WO | WO 2004/037111 A1 * | 5/2004 |

\* cited by examiner

*Primary Examiner*—Cris L Rodriguez
*Assistant Examiner*—Sunil K Singh
(74) *Attorney, Agent, or Firm*—Steven A. Bern (57) ABSTRACT

The present invention relates to the production of dental replacement using a CAD system. In particular, the present invention relates to the design of the three-dimensional shape of a dental prosthesis, which has, for example, two prosthesis sections and a connector section, the connector section being connected to the two prosthesis sections.

27 Claims, 12 Drawing Sheets

METHOD AND SYSTEM FOR DESIGNING A DENTAL REPLACEMENT

FIELD OF THE INVENTION

The present invention relates to the production of dental replacements using a CAD (Computer-Assisted Design) system. In particular, the present invention relates to the design of the three-dimensional shape of a dental prosthesis, which has, for example, two prosthesis sections and a connector section, which is connected to the two prosthesis sections.

BACKGROUND

The processing of data regarding the three-dimensional shape of a dental replacement may be done by means of a CAD (computer-aided design) system, which may be part of a CIM (computer-integrated manufacturing) system. Such systems are made available, for example, by 3M ESPE AG (Seefeld, Germany) under the name LAVA™, for the production of ceramic bridge copings. With this known LAVA™ system, the CAD system is connected to an optical scanner and to an NC-milling machine. The scanner captures the three-dimensional surface of a dentition impression and passes on the captured data to the CAD system. Using the CAD system, the operator can modify these surface data as desired, so as to draw up the three-dimensional shape of the bridge coping, calculate CNC data from the shape data using CAM software, and then send the corresponding CNC data to the NC-milling machine. The NC-milling machine then processes, for example, a zirconium oxide or zirconia ceramic blank as precisely as possible in agreement with the shape data.

At a dentist, an impression is produced from the situation in the mouth of the patient. This impression is used by a dental technician to prepare a positive saw cut model of the situation in the patient's mouth. The positive model is typically made from gypsum or light plaster. This positive model thus corresponds to the teeth in the patient's mouth. Conventionally, the positive model is then sent to a milling center where it is scanned and milled, as described above.

In some situations, e.g., with a 4-unit bridge, it is often difficult for the technician in the milling center to determine the exact and optimal position and dimension of the bridge units as well as the necessary reinforcement or the correct arrangement of the copings. This is, however, an important factor for an optimal facing with veneer porcelain in terms of stability, function, and aesthetics. If the positioning of the bridge units is not correct, the design of the dental replacement may need to be reworked, e.g. virtually modified in the milling center, and a new replacement milled, which can add considerably to the cost of producing the replacement.

SUMMARY OF THE INVENTION

The present invention features a method and system for designing a dental replacement.

In a first aspect, the present invention provides a method for designing a dental replacement from at least one bridge pontic model, the method comprising the steps of: scanning the at least one bridge pontic model to obtain a first set of three-dimensional image data; scanning at least a part of a positive model of the dental situation of the patient to obtain a second set of three-dimensional image data; calculating a virtual three-dimensional model of the dental replacement on the basis of the first and second sets of three-dimensional image data; and modifying the calculated virtual three-dimensional model of the dental replacement with reference to the first and second sets of three-dimensional image data.

The at least one bridge pontic model can be made from a suitable formable dental material, such as plastics or wax. The at least one bridge pontic model is typically a semi wax up model. Alternatively, a previous or provisional dental replacement can be used as bridge pontic model.

In one embodiment of the invention, a model of at least one die or tooth stump adjacent to the at least one bridge pontic model is the part of the positive model that is scanned. Typically, two dies are scanned.

The method optionally further comprises the step of scanning at least one directly adjacent tooth of the positive model to obtain a third set of three-dimensional image data. The third set of three-dimensional image data can be used for modifying the calculated three-dimensional model. Typically, the at least one adjacent tooth is scanned concurrently with the at least one bridge pontic model in the first scanning step.

The calculating step typically comprises calculating the three-dimensional model of the bridge pontic and of the adjacent copings of the dental replacement.

The modifying step typically comprises a step of displaying the units of the calculated three-dimensional model of the dental replacement on a display, a step of displaying the image of the scanned bridge pontic model, and a step of moving the bridge pontic of the calculated three-dimensional model of the dental replacement in at least one of x-, y-, or z-direction to its optimal position with reference to the scanned bridge pontic model. Alternatively or additionally, the modifying step further comprises the step of scaling the calculated bridge pontic in at least one of x-, y-, or z-direction with reference to the scanned bridge pontic model.

The step of modifying the calculated three-dimensional model of the dental replacement typically also involves the steps of displaying the image of the scanned adjacent tooth model, and scaling the calculated bridge pontic in at least one of x-, y-, or z-direction with reference to the scanned adjacent tooth model. The modifying step typically further includes the step of removing or adding material to the calculated bridge pontic. Finally, it is also possible to rotate the calculated bridge pontic around at least one of x-, y-, or z-axis.

It is also possible to scan a model of the ridge in the area of the dental replacement to obtain a fourth set three-dimensional image data, wherein the three-dimensional model of the dental replacement is modified also using the fourth set of three-dimensional image data representing the scanned ridge.

According to one embodiment of the invention, the three-dimensional model of the dental replacement is calculated using a library of bridge units. In a subsequent step, the connections between the bridge units can be determined and positioned. Finally, the holding pins for holding the milled dental replacement in the material blank, for example all-ceramic, can be determined and positioned between the units.

In certain embodiments of the present invention, it is preferred to provide the bridge pontic model as a semi wax up model or pre-wax up model.

In a second aspect of the present invention, a method for designing a dental replacement from a bridge frame model is provided. The bridge frame model is typically prepared from wax by a dental technician. Alternatively, other suitable formable dental materials such as plastics can be used. In yet another alternative, a previous or provisional dental replacement is used as bridge frame model. The method according to the second aspect of the invention comprises the steps of: scanning the bridge frame model to obtain a first set of three-dimensional image data; scanning at least a part of a positive model of the dental situation of the patient to obtain a second set of three-dimensional image data; calculating a virtual three-dimensional model of the dental replacement on the basis of the first and second sets of three-dimensional image data; and modifying the calculated three-dimensional model of the dental replacement using the first and second set of three-dimensional image data. Typically, the step of calculating a three-dimensional model of the dental replacement comprises calculating the three-dimensional model of the bridge frame and of the adjacent copings of the bridge frame.

Typically, a model of at least one die or tooth stump onto which the dental replacement is to be placed is scanned as the part of the positive model. More typically, two dies are scanned.

The method may optionally further comprises the step of scanning at least one directly adjacent tooth of the positive model to obtain a third set of three-dimensional image data. This third set of three-dimensional image data is used in addition for modifying the calculated three-dimensional model. Typically, the at least one adjacent tooth is scanned concurrently with the at least one bridge frame model in the first scanning step.

The modifying step typically comprises a step of displaying the units of the calculated three-dimensional model of the bridge frame on a display, a step of displaying the image of the scanned bridge frame model, and a step of moving the bridge frame of the calculated three-dimensional model of the dental replacement in at least one of x-, y-, or z-direction to its optimal position with reference to the scanned bridge frame. More typically, the modifying step also comprises the step of scaling the calculated bridge frame in at least one of x-, y-, or z-direction with reference to the scanned bridge frame model. It is additionally possible that the modifying step comprises scaling the calculated bridge copings in at least one of x-, y-, or z-direction with reference to the scanned bridge model.

The method according to the second aspect typically further comprises the steps of displaying the image of the scanned adjacent tooth model, of scaling the calculated bridge frame in at least one of x-, y-, or z-direction with reference to the scanned adjacent tooth model, and of scaling the calculated copings in at least one of x-, y-, or z-direction with reference to the scanned adjacent tooth model.

The method of the second aspect of the present invention may also further comprise the step of rotating the calculated bridge frame around at least one of x-, y-, or z-axis.

According to another embodiment, the method of the present invention comprises the step of virtually removing or adding material to the calculated bridge pontic, bridge frame, and/or copings. With a CAD-system, material can be removed or added with, for example, an artificial/virtual wax knife.

The calculated three-dimensional model of the dental replacement is typically modified in the modifying step such that a uniform thickness of the veneer of the dental replacement is achievable after milling and sintering of the dental replacement in case of an all-ceramic material.

In a further embodiment, the method of the second aspect of the invention comprises the step of scanning a model of the ridge in the area where the dental replacement is to be located to obtain a fourth set of three-dimensional image data, wherein the three-dimensional model is modified also using the fourth set of three-dimensional image data.

The method of the second aspect of the present invention may also include the calculation of the three-dimensional model of the dental replacement using a library of bridge units.

Optionally, the method of the second aspect of the present invention further comprises the step of determining and positioning the connections between the bridge units, and comprises the step of determining and positioning the holding pins for holding the milled dental replacement in the material blank, for the case that the dental replacement is, for example, made from a ceramic or all-ceramic material.

It is preferred in all aspects of the present invention that for modifying the calculated three-dimensional model of the dental replacement input signals from a keyboard and/or computer mouse are utilized.

According to a third aspect of the present invention, a method for designing a dental replacement from at least one bridge pontic model is provided. The method according to the third aspect comprises the steps of: providing first input data representing a three-dimensional surface of the at least one bridge pontic model; providing second input data representing a three-dimensional surface of at least a part of a positive model of the dental situation of the patient; processing the first and second input data for displaying the three-dimensional surface of the at least one bridge pontic model and the part of the positive model on a display; calculating a three-dimensional model of the dental replacement on the basis of the first and second input data; displaying the three-dimensional model of the dental replacement on the display; and modifying the calculated three-dimensional model of the dental replacement with reference to the three-dimensional surface of the at least one bridge pontic model and the part of the positive model. Typically, the first input data are obtained by scanning the at least one bridge pontic model with a scanner, for example an optical scanner. In addition, the first input data also typically comprise data of at least one scanned adjacent tooth.

According to a fourth aspect of the present invention, a method for designing a dental replacement from a bridge frame model is provided. The method according to the fourth aspect comprising the steps of: providing first input data representing a three-dimensional surface of the bridge frame model; providing second input data representing a three-dimensional surface of a part of a positive model of the dental situation of the patient; processing the first and second input data for displaying the three-dimensional surface of the bridge frame model and the part of the positive model on a display; calculating a three-dimensional model of the dental replacement on the basis of the first and second input data; displaying the three-dimensional model of the dental replacement on the display; and modifying the calculated three-dimensional model of the dental replacement with reference to the three-dimensional surface of the bridge frame model and the part of the positive model. Typically, the first input data are obtained by scanning the bridge frame model with a scanner. Often the first input data also comprise data of at least one scanned adjacent tooth.

According to a fifth aspect, the present invention provides a system for designing a dental replacement from at least one bridge pontic model. The system comprises a first input means for providing first input data representing a three-dimensional surface of the at least one bridge pontic model, and for providing second input data representing a three-dimensional surface of at least a part of a positive model of the dental situation of the patient; a processor for processing the first and second input data for displaying the three-dimensional surface of the at least one bridge pontic model and the part of the positive model on a display, wherein the processor calculates a three-dimensional model of the dental replacement on the basis of the first and second input data and for displaying the three-dimensional model of the dental replacement on the display; and a second input means for inputting modification instructions for modifying the calculated three-dimensional model of the dental replacement with reference to the three-dimensional surface of the at least one bridge pontic model and the part of the positive model.

In accordance with a sixth aspect of the present invention, a system for designing a dental replacement from a bridge frame model comprises a first input means for providing first input data representing a three-dimensional surface of the bridge frame model, and for providing second input data representing a three-dimensional surface of at least a part of a positive model of the dental situation of the patient; a processor for processing the first and second input data for displaying the three-dimensional surface of the bridge frame model and the part of the positive model on a display, wherein the processor calculates a three-dimensional model of the dental replacement on the basis of the first and second input data and for displaying the three-dimensional model of the dental replacement on the display; and a second input means for inputting modification instructions for modifying the calculated three-dimensional model of the dental replacement with reference to the three-dimensional surface of the bridge frame model and of the part of said positive model.

Typically, the first input means of the systems of the fifth or sixth aspect comprises a scanner. Preferably, the second input means comprises a keyboard and/or a computer mouse.

In accordance with a seventh aspect of the present invention, a dental replacement being designed according to the method of any of the first through fourth aspects is provided.

In accordance with an eighth aspect of the present invention, a computer program product means is provided comprising program code stored thereon being capable when run on a computer to perform the method of any of the first through fourth aspects.

The present invention provides a substantial advancement in the design of dental replacements with a CAD-system since the design and positioning of the pontic is substantially easier with the methods of the present invention. It is sufficient for the dental technician to prepare a waxup of the bridge frame or of the final situation in the patient's mouth, or to prepare a pontic model, for example a wax pontic, on the ridge of the prepared saw cut model. This is, however, only taken as orientation for the design of the copings or for the positioning of the bridge pontics but is not taken into account for calculating the final milling data. Therefore, it is not required to precisely adapt the borderline of the model. Thus, communication between the dental laboratory and the milling center is optimized, and the design of the virtual construction of the dental replacement in the milling centre can be done in substantially reduced time.

Furthermore, it is no longer necessary to prepare and provide a bite registration of the patient. Instead, the waxup or the wax bridge pontics and preferably the ridge and adjacent teeth can be scanned and used for designing the dental replacement. This reduces scanning time because no bite registration needs to be scanned.

The present invention uses a virtual knife function, e.g., a wax knife function, provided by the design system to apply or remove material from the calculated bridge, and/or to position or scale the bridge.

As used herein, the term "dental prosthesis" is to be understood to include all types of dental replacements, such as, for example, bridges (e.g., multi-unit bridges), implants, and dental prostheses. The term also refers to parts of such dental prostheses, such as, for example, bridge substructures or copings onto which a veneering must still be applied in order to obtain the finished bridge.

The quantity indications used herein, such as, for example, "two prosthesis sections" or "a connector section", are in general to be understood as a minimum, with the meaning of "at least two" or "at least one", unless the limitation is expressed by wording such as "exactly" or "consisting of".

The present invention thus includes, for example, not only two-unit bridge copings where the two units are connected by one connector, but also three- and multi-unit bridge copings, where each two adjacent units are connected by one connector. The units may be, as needed, anchors, intermediate units also called pontics, or cantilever units. An anchor is fastened like a crown, on a tooth stump serving as a bridge abutment. An intermediate unit or pontic is fastened between two units and not to a bridge abutment. A cantilever unit is fastened only to one unit and not to a bridge abutment.

With a one-piece bridge, i.e., a bridge that consists of one single piece and has no coping, adjacent bridge units border directly against one another, without a connector lying in between. In this case, the transition area from one unit to the other represents the connector section of the present invention, the transition area having a more or less prominent restriction or flattening due to the shape of the units that are intended to come as close as possible to the natural appearance of the missing teeth.

Other features and advantages of the present invention will be apparent from the following detailed description thereof, and from the drawings and claims.

BRIEF DESCRIPTION OF THE DRAWINGS

The present invention will be described in more detail in the following with reference to the drawings in which.

DETAILED DESCRIPTION

FIGS. 1a to 1i show a scenario of designing a dental replacement according to a first embodiment of the invention. More specifically, the first embodiment relates to the preparation of a dental replacement for the upper jaw.

Figure 1A:
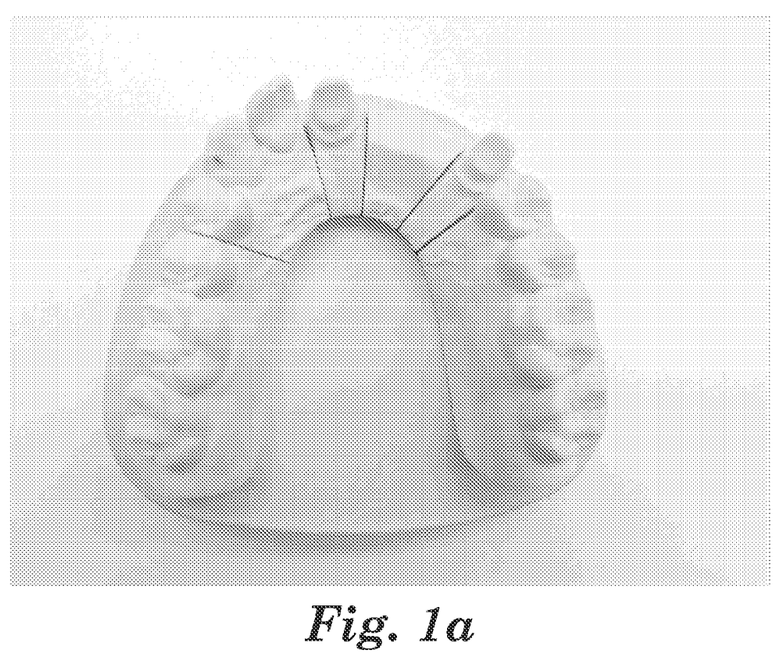
FIGS. 1a to 1i show a first embodiment of the present invention, i.e., a method for designing a dental replacement from at least one bridge pontic model.
Figure 1B:
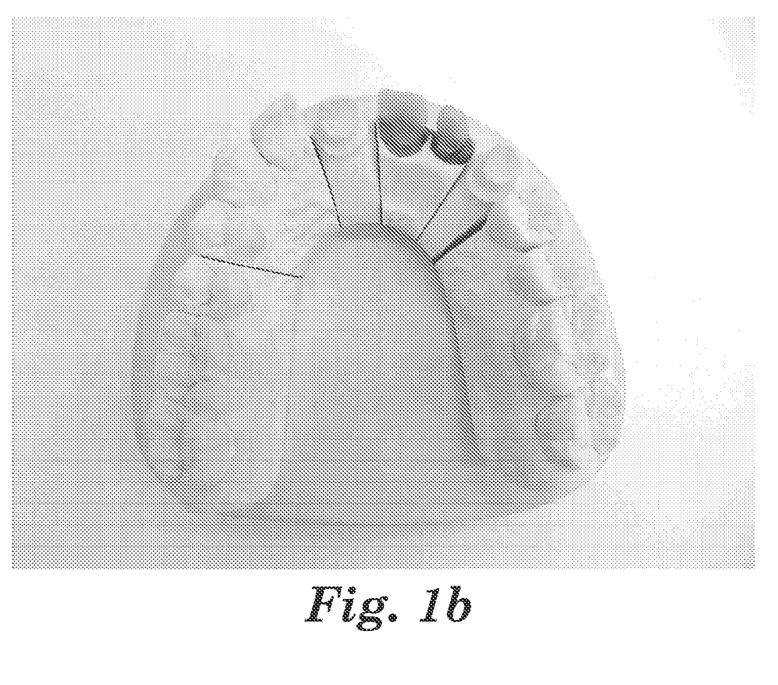

In FIG. 1a, an example of a typical situation of a patient's upper jaw is shown in the form of a positive saw cut model that has been prepared by, for example, a dental technician. It shows the ridge where two teeth are missing, as well as the two dies adjacent to the ridge. FIG. 1b shows the same saw cut model, together with the two bridge pontic models, typically made from wax, that have been selected by the dental technician (for example from a "library" of different samples of bridge pontic models) and fixed to the saw cut model. Typically, the two wax models are fixed to the saw cut model by the dental technician in an arbitrary orientation; rather, the dental technician at this stage usually makes an attempt to fix the two rough wax models in an orientation that matches or is at least close to the desired orientation of the artificial teeth to be prepared. Thus, the dental technician generally gives the technician in the milling center guidance as to how the dental replacement has to be designed using the CAD-system.

Figure 1C:
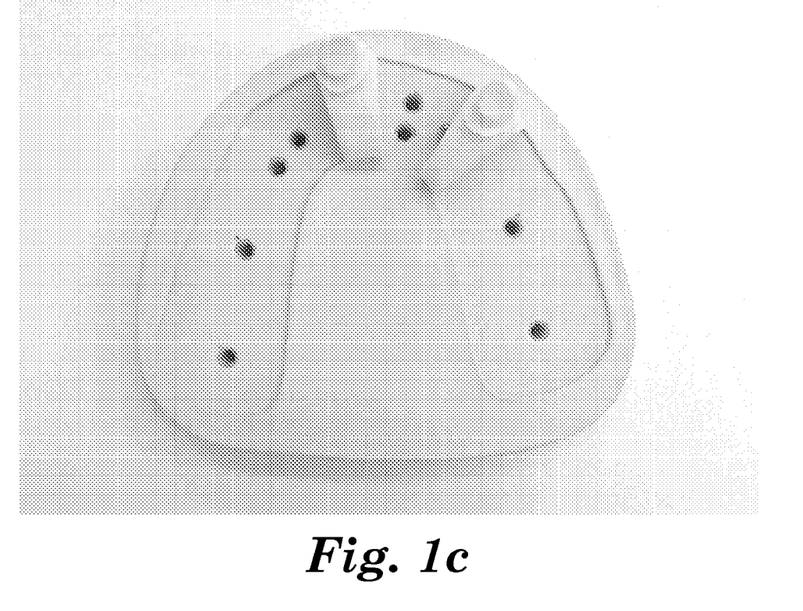
Figure 1D:
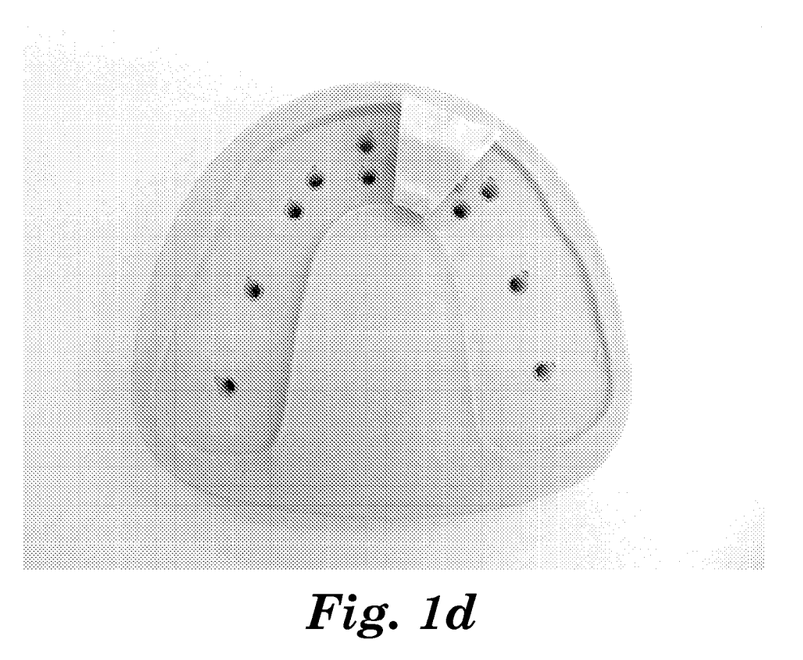
Figure 1E:
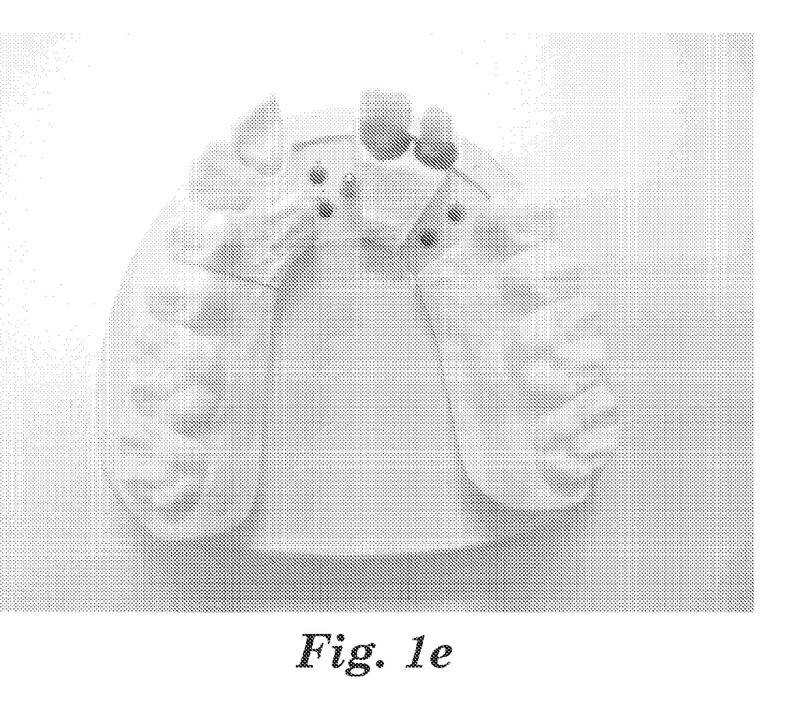

FIGS. 1c to 1e show different components of the saw cut model. FIG. 1c shows the two dies alone with, the models of the ridge and of the adjacent teeth having been removed from the saw cut model in this depiction. FIG. 1d shows the ridge alone, and FIG. 1e shows the saw cut model with the ridge having the wax models fixed onto it, and the adjacent teeth.

According to a typical procedure, the two dies (FIG. 1c), the ridge (FIG. 1d), and the bridge pontic models along with the adjacent teeth (FIG. 1e) are scanned in three separate steps. However, the present invention is not limited to the scanning of these three different components. In its broadest aspect of the present invention, only the bridge pontic models as well as the adjacent teeth are scanned (FIG. 1e) and not necessarily simultaneously.

Figure 1F:
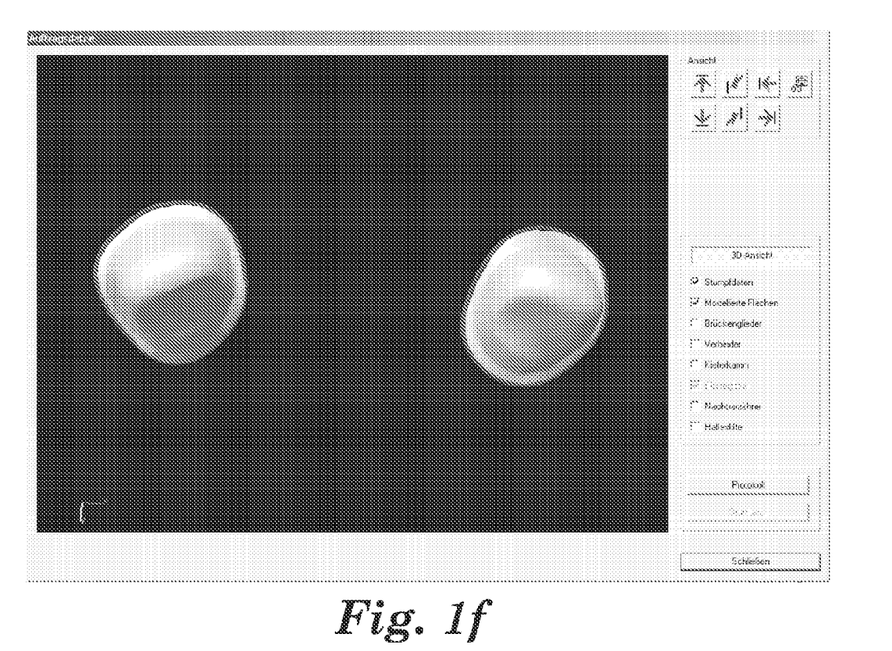
Figure 1G:
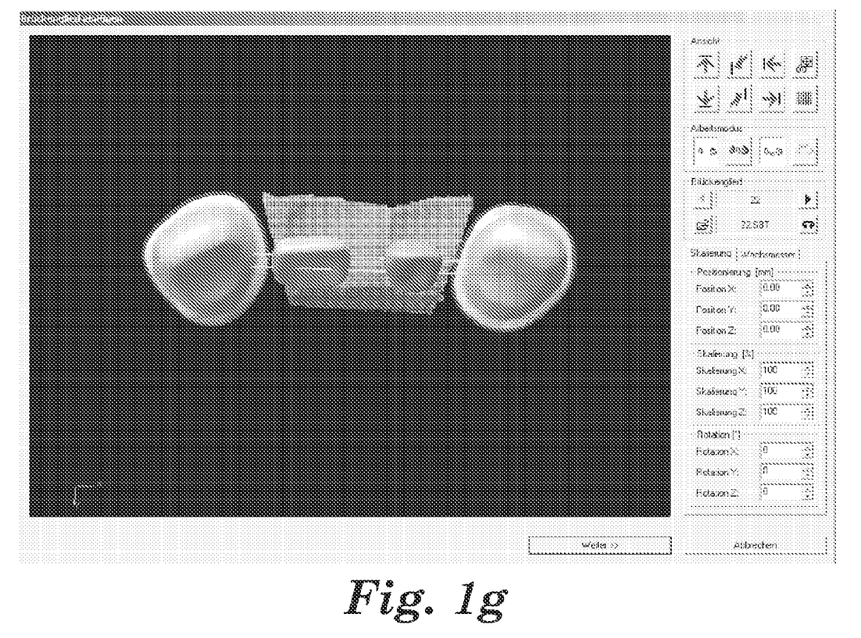

FIG. 1f shows how the scanned dies are depicted on a display. In FIG. 1g, the scanned ridge is shown in addition to the scanned dies. Furthermore, FIG. 1g already shows the calculated three-dimensional model of the dental replacement being placed between the images of the two dies and above the ridge.

Figure 1H:
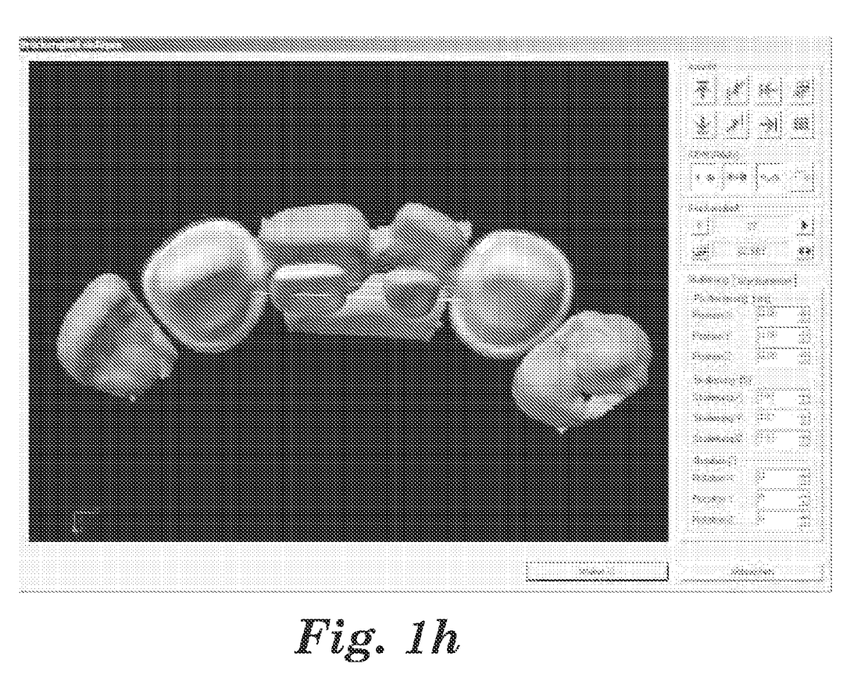
Figure 1I:
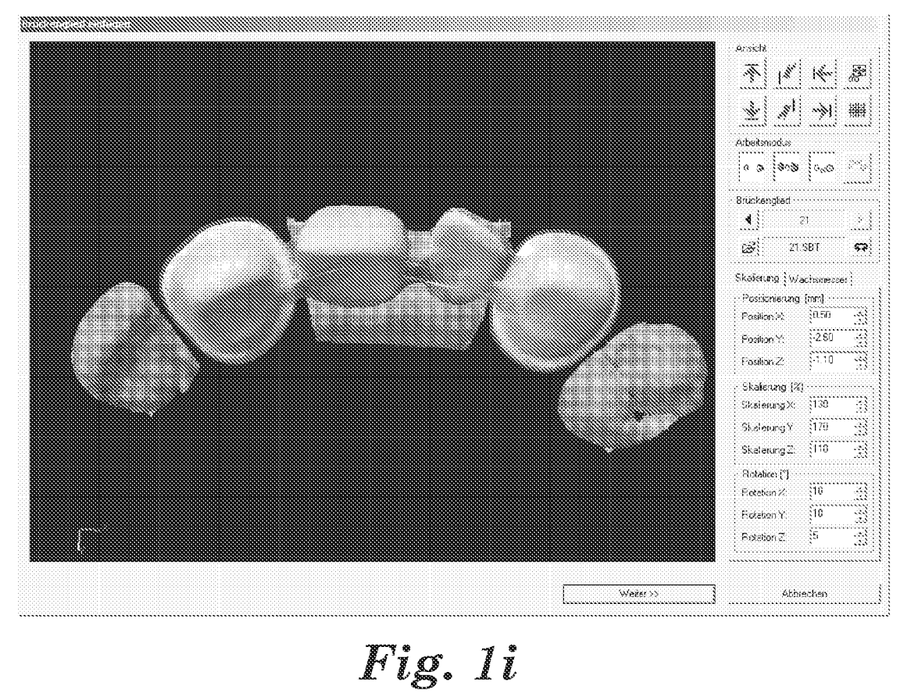

In addition to the images of the two dies, the ridge, and the calculated three-dimensional model of the dental replacement, FIG. 1h shows the image of the scanned bridge pontic models and the image of the two (left and right) adjacent teeth. Thus, this picture shows the user of the system the optimum position of the prosthesis (namely, the image of the canned bridge pontic model) and how the calculated proposal actually deviates from the optimum position and orientation. Then, the user changes the position, orientation and scale of the calculated prosthesis until it matches or coincides with the optimum prosthesis arrangement (see FIG. 1i). Since the two adjacent teeth are also displayed, their position, orientation, size, and shape is also used for modifying the calculated prosthesis until it has its desired form.

FIGS. 2a to 2m show a scenario of designing a dental replacement according to a second embodiment of the invention. Specifically, the second embodiment relates to the preparation of a dental replacement for the lower jaw, namely a 4-unit bridge.

Figure 2A:
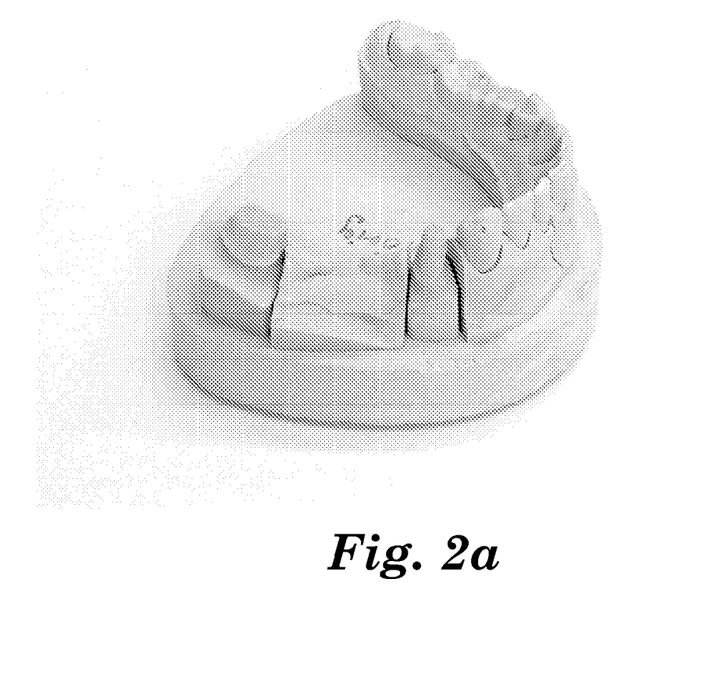
FIGS. 2a to 2m show a second embodiment of the present invention, i.e., a method for designing a dental replacement from a bridge frame model.
Figure 2B:
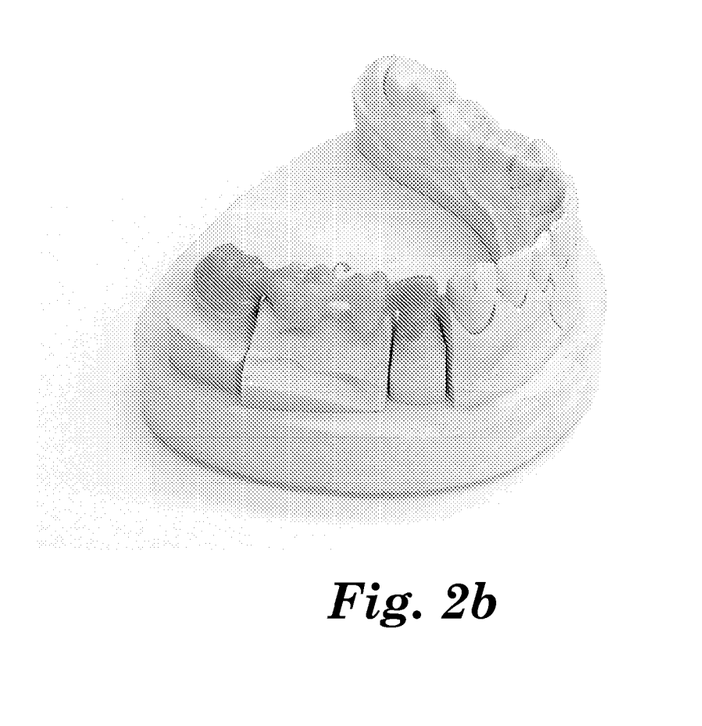

In FIG. 2a, an example of a typical situation of a patient's lower jaw is shown in form of a positive saw cut model that has been prepared, for example, by a dental technician. FIG. 2a shows the ridge where two teeth are missing, as well as the two dies adjacent to the ridge. FIG. 2b shows the same saw cut model, with the addition of the bridge frame models, typically made from wax (i.e., a so called wax up), that has been prepared, for example, by a dental technician and attached to the saw cut model. In this example, the bridge frame model prepared, for example, by a dental technician is quite detailed since the thickness of the copings that are to be placed on the existing dies is a decisive factor. This thickness is typically determined by the dental technician. When selecting the thickness of the coping the thickness of the final veneer has to be considered. The veneer must not be too thick because it easily cracks; on the other hand, there has to be sufficient space for a minimum veneer thickness. If a minimum veneer layer thickness is not given by the bridge frame model prepared by the dental technician, the thickness of the frame can be reduced when the final shape of the bridge frame is designed.

Figure 2C:
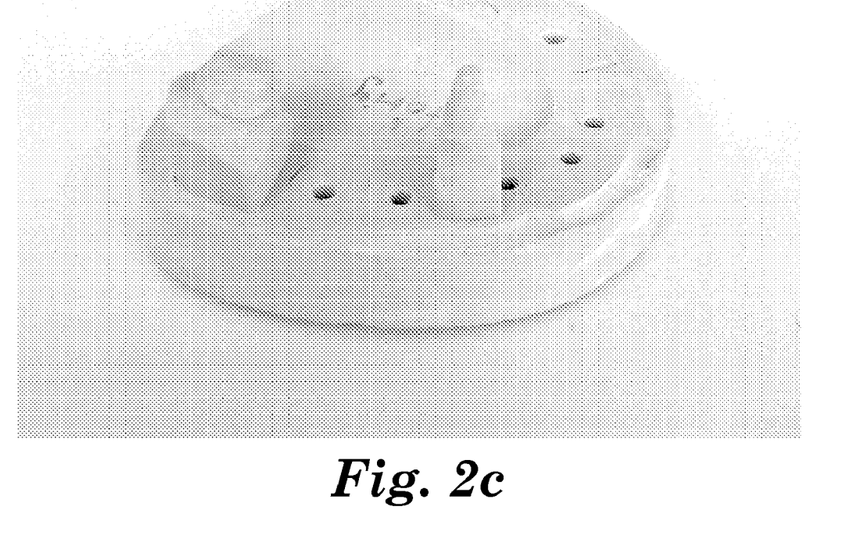
Figure 2D:
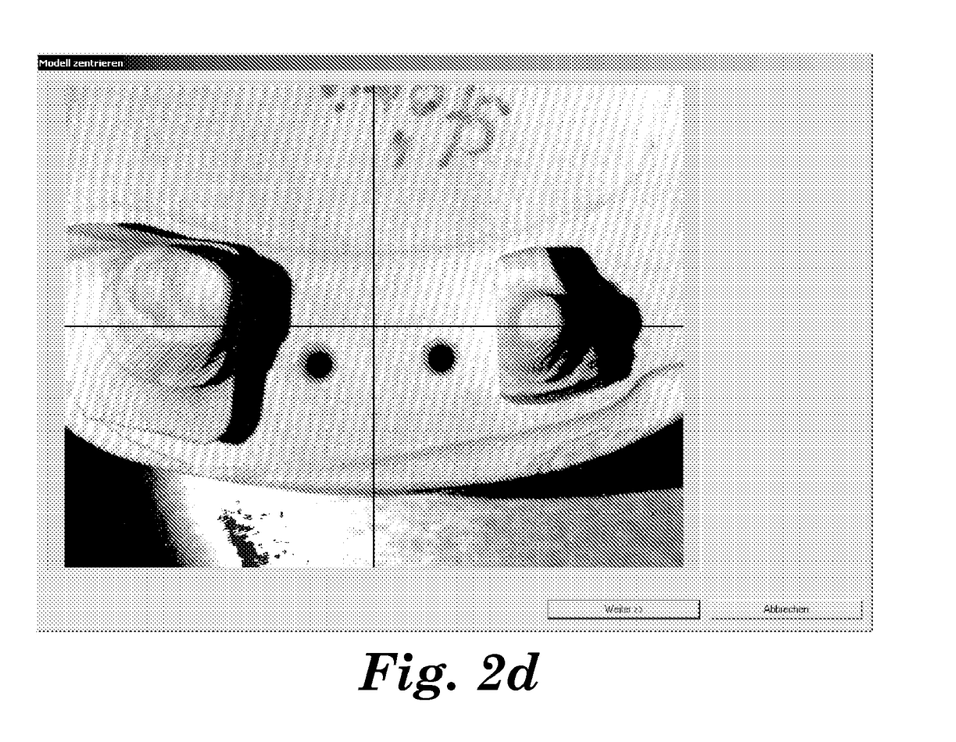

FIG. 2c shows the two dies adjacent to the ridge where the teeth are missing. Once the two dies have been scanned, their images can be displayed as shown in FIG. 2d.

Figure 2E:
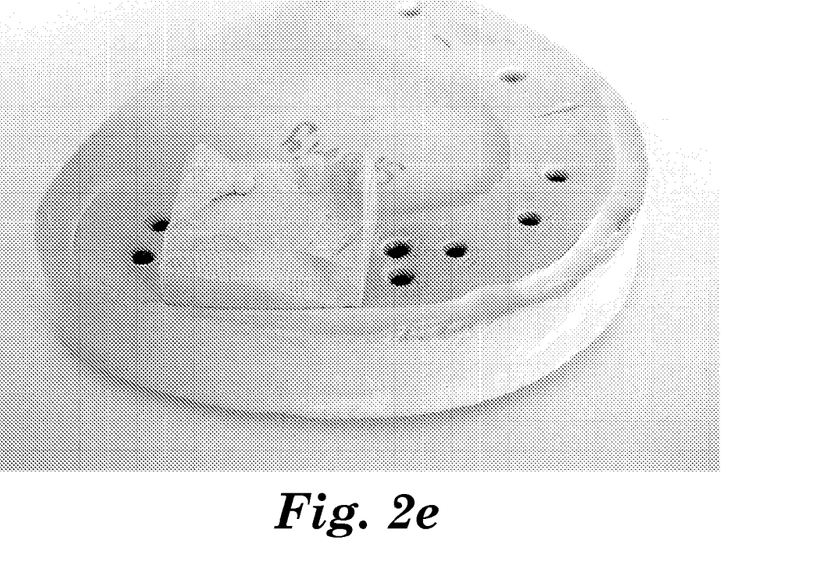
Figure 2F:
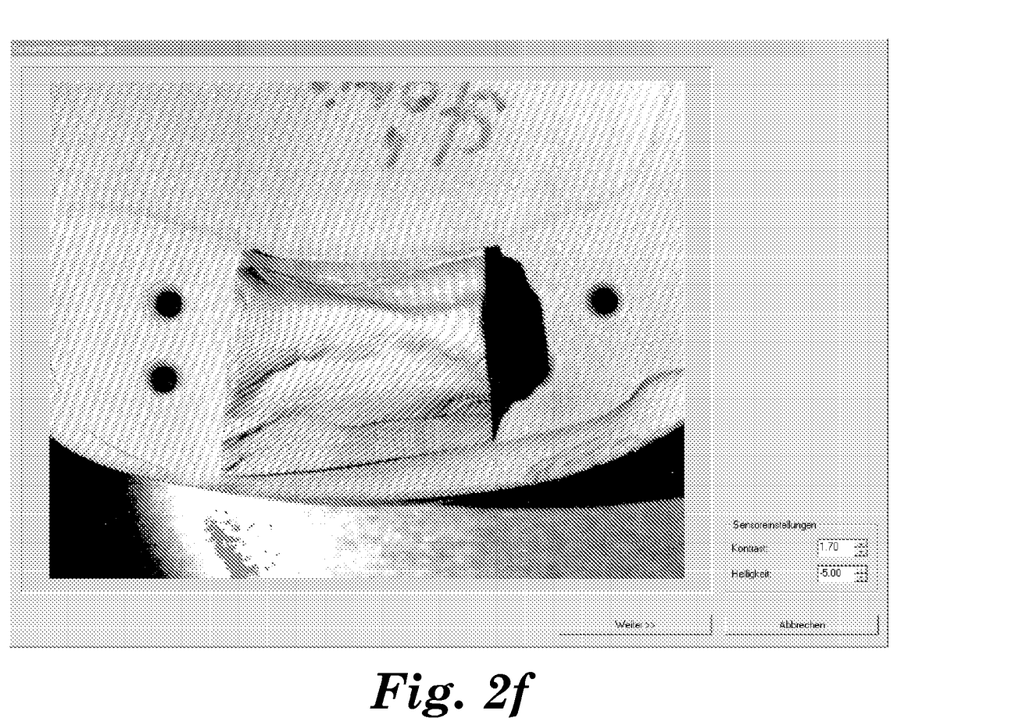

In FIG. 2e, only the ridge part of the lower jaw where the teeth are missing of the saw cut model is shown. FIG. 2f shows how the scanned ridge is displayed on the display of the CAD-system.

Figure 2G:
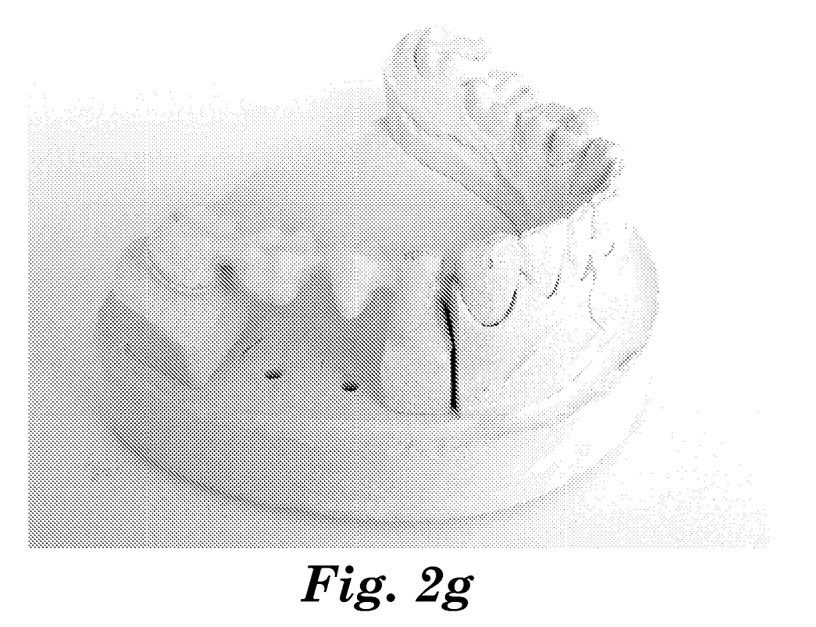
Figure 2H:
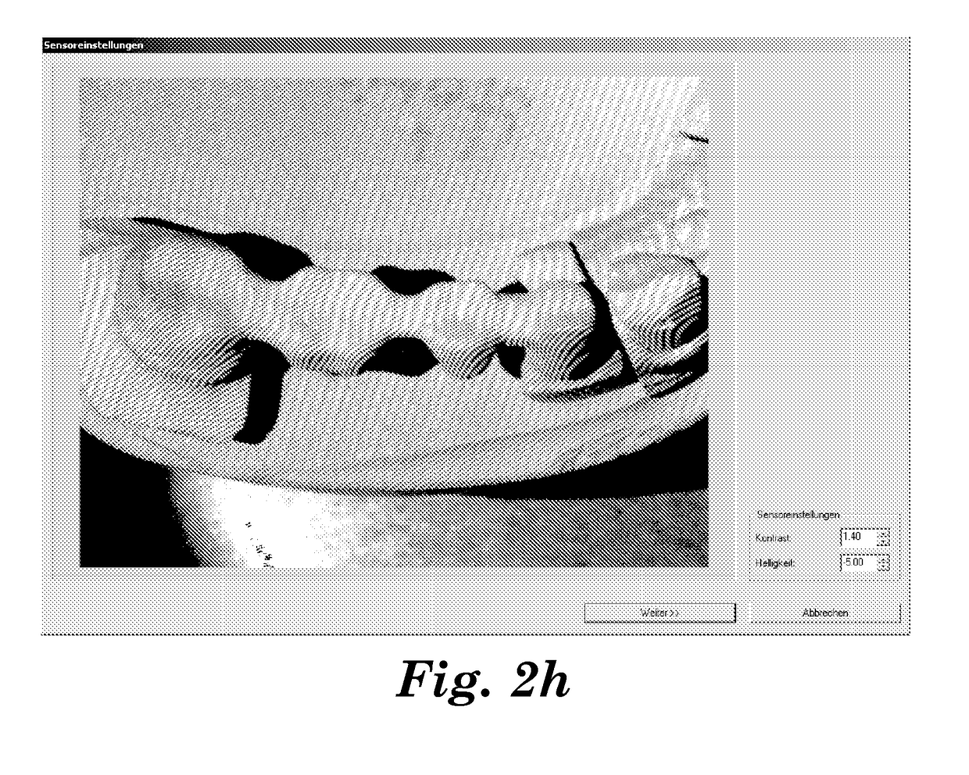

FIG. 2g shows the bridge frame model placed onto the dies of the saw cut model but without the ridge underneath. The image of this arrangement after scanning is shown in FIG. 2h. FIG. 2h shows that not only the bridge frame model has been scanned but also the adjacent tooth. In the embodiment shown in FIG. 2 the bridge frame has only one adjacent tooth, i.e. the right tooth in FIGS. 2h and 2i. However, the method would work in situations where there is more than one adjacent tooth.

Figure 2I:
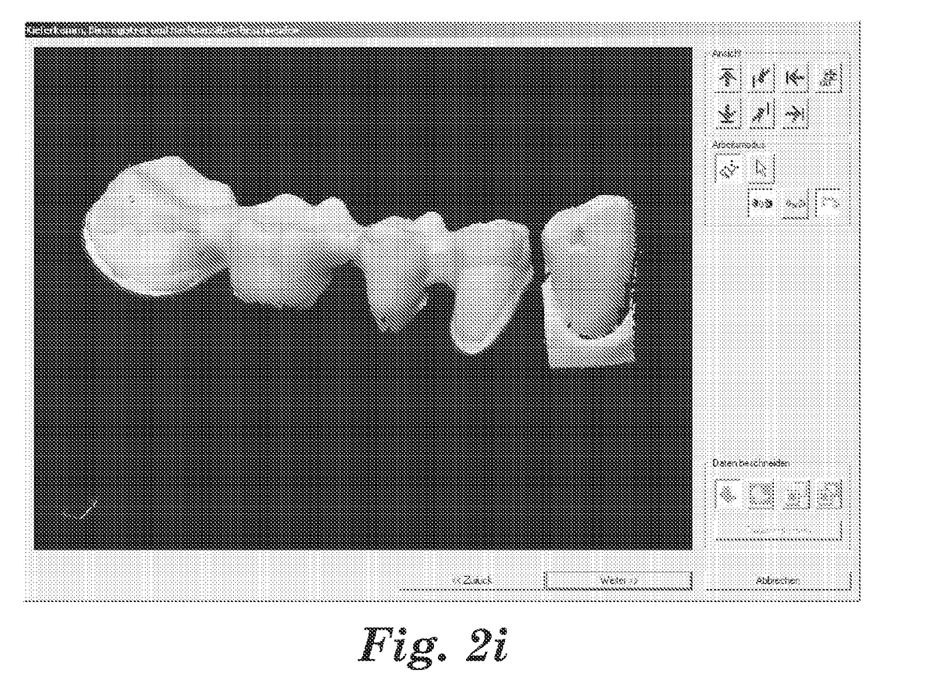

After scanning, the scanned bridge frame model is then modified on the CAD-system using, for example, an artificial knife, e.g. a wax knife, in order to obtain the final desired shape and size of the bridge frame model. The shape and size of the adjacent tooth or teeth may also be considered. As shown in FIG. 2i, first the bridge pontics are designed, like in the embodiment of FIG. 1.

Figure 2J:
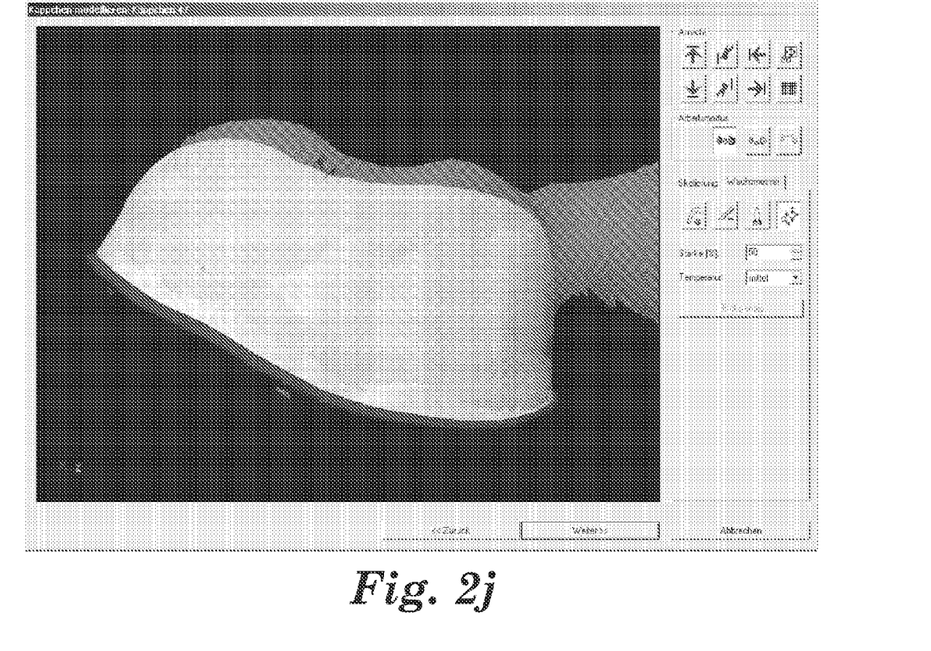
Figure 2K:
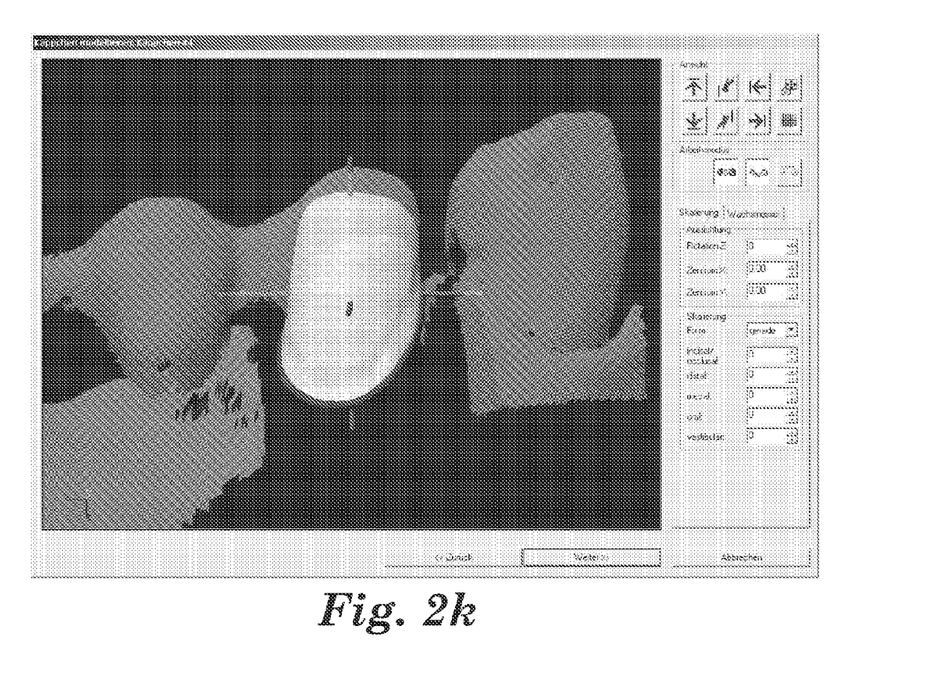

FIGS. 2j and 2k show how the copings for the two dies can be modified and shaped as desired (for example FIG. 2j for the molar, and FIG. 2k for the canine). Specifically, the calculated copings can be displayed together with the scanned copings so that the user is provided with a guidance as to how the calculated copings need to be modified (for example, upscaled, down-scaled, rotated, inclined, etc.) in order to finally match the appropriate shape. According to the present invention, the scanned adjacent teeth can also be displayed during this step so that the size and shape of the adjacent teeth are considered when modifying the copings of the bridge frame.

Figure 2L:
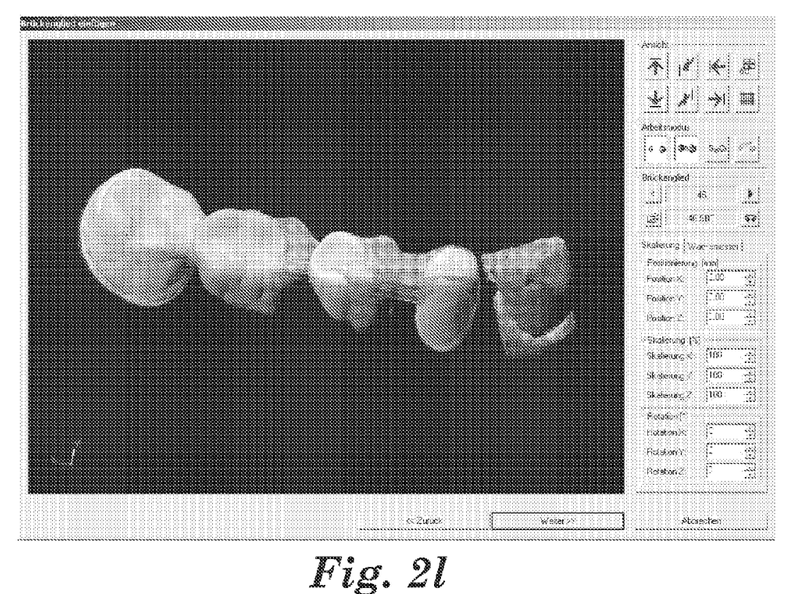

In FIG. 2l, the virtual connectors between the prosthesis sections are added and positioned as desired. In this step, it is also possible to ensure that stability parameters of the connectors are within required ranges so that the connectors do not break during milling, sintering, or veneering of the bridge, if made from a ceramic material, for example.

Figure 2M:
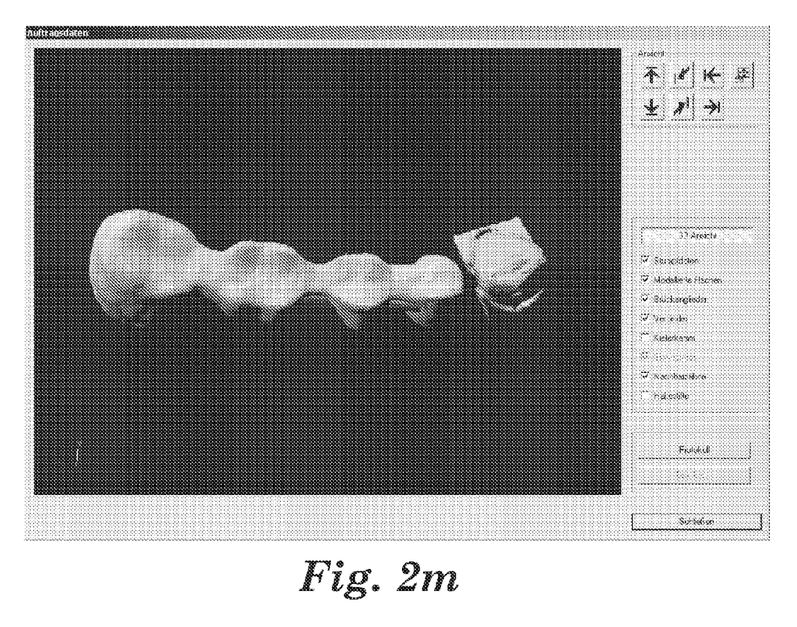

A virtual bridge frame being optimally positioned and dimensioned according to the present invention is shown in FIG. 2m.

When the modifications to the prosthesis are completed, the data of the final prosthesis are used for manufacturing, for example milling, of the prosthesis. In case the prosthesis is milled from a ceramic material, e.g., all-ceramic, the milled prosthesis is sintered, and then sent to the dental technician who finally applies the veneer.

Although specific embodiments of the present invention have been described above in detail, it will be understood that this description is merely for purposes of illustration. Various modifications of and equivalents corresponding to the disclosed aspects of the preferred embodiments described above may be made by those skilled in the art without departing from the spirit of the present invention, which is defined by the following claims.

What is claimed is:

1. A computer-implemented method for designing a dental replacement from at least one bridge pontic model, comprising the steps of:
   a) receiving first three-dimensional image data from scanning the at least one bridge pontic model;
   b) receiving second three-dimensional image data from scanning at least a part of a dental situation of a patient, the scanned part of the dental situation of the patient including at least one missing tooth and at least one tooth adjacent to the missing tooth;
   c) receiving third three-dimensional image data defining the dental replacement, the dental replacement including at least one virtual pontic;
   d) calculating in a computer a virtual three-dimensional model using the first, second, and third three-dimensional image data wherein the first, second, and third three-dimensional image data is visually combined in a display such that the virtual three-dimensional model is a representation of the patient's dental situation with the bridge pontic model and the dental replacement shown in a location proximate to the patient's missing tooth;

e) receiving modification data from a user with respect to the virtual three-dimensional model, wherein the modification data comprises at least instructions to scale the dental replacement in the x-, y-, or z-directions, with reference to the pontic model and virtually remove or add material to the dental replacement; and, f) modifying the virtual three-dimensional model based on the modification data.

2. The method of claim 1, wherein receiving modification data comprises receiving input to a computer via a keyboard and/or pointing device.

3. The method of claim 1, wherein scanning at least a part of a dental situation of a patient is accomplished by scanning a positive or negative model of the patient's dental situation.

4. The method of claim 1, wherein the at least one bridge pontic model is made from plastic or wax.

5. The method of claim 1, wherein modification data comprises instructions to cause the dental replacement to be scaled in size, relative to the bridge pontic model.

6. The method of claim 1, wherein the dental situation of the patient includes at least one die adjacent to the at least one bridge pontic model.

7. The method of claim 6, wherein calculating a three-dimensional model further comprises calculating, for the at least one adjacent die, dimensions of copings for the dental replacement.

8. The method of claim 1, wherein modification data comprises instructions to cause the dental replacement to move in one of x-, y-, or z-directions, relative to the bridge pontic model.

9. The method of claim 1, wherein the third three-dimensional image data is received from a library that contains data defining at least two dental replacements.

10. The method of claim 1, wherein the dental situation of the patient includes a ridge and wherein the scanned part of the dental situation of the patient further includes the ridge.

11. The method of claim 1, further comprising displaying the virtual three-dimensional model.

12. The method of claim 1, wherein modification data comprises instructions to cause rotation of the dental replacement model around at least one of the x-, y-, or z-axis.

13. The method of claim 1, wherein calculating the virtual three-dimensional model further includes determining and positioning at least one virtual holding pin for holding a milled dental replacement in a material blank.

14. A computer-implemented method for designing a dental replacement from a bridge frame model, comprising the steps of:

a) receiving first three-dimensional image data from scanning the bridge frame model;

b) receiving second three-dimensional image data from scanning at least a part of a dental situation of a patient, the scanned part of the dental situation of the patient including at least two stumps adjacent one another;

c) calculating in a computer third three-dimensional image data defining the dental replacement, the dental replacement including coping layer defined by an exterior surface and an interior surface, the interior surface approximating a negative of one of the two stumps;

d) calculating in the computer a virtual three-dimensional model using the first, second, and third three-dimensional image data wherein the first, second, and third three-dimensional image data is visually combined in a display communicatively coupled to the computer such that the virtual three-dimensional model is a representation of the patient's dental situation with the bridge frame model and the dental replacement shown in a location proximate to the patient's stumps; and e) receiving modification data with respect to the virtual three-dimensional model, wherein the modification data comprises instructions to cause rotation of the dental replacement model around at least one of the x-, y-, or z-axis and, if a coping layer exists as part of the dental replacement model, instructions to cause virtual removing or adding of material to the dental replacement's coping layer; and, f) modifying the virtual three-dimensional model based on the modification data.

15. The method of claim 14, wherein the modification data comprises instructions to alter the dental replacement relative to the first and second three-dimensional data.

16. The method of claim 14, wherein scanning at least a part of a dental situation of a patient is accomplished by scanning a positive or negative model of the dental situation of a patient.

17. The method of claim 16, wherein the bridge frame model is a plastics or wax model.

18. The method of claim 14, wherein the scanned part of the dental situation or the patient further includes at least one die onto which the dental replacement is to be placed.

19. The method of claim 14, wherein the scanned part of the dental situation of the patient further includes at least one tooth adjacent to either of the at least two stumps.

20. The method of claim 14, wherein calculating third three-dimensional image data further includes calculating dimensions of copings adjacent to the bridge frame.

21. The method of claim 14, wherein modification data comprises instructions to cause the dental replacement to move in one of x-, y-, or z-directions relative to the scanned bridge frame model.

22. The method of claim 14, wherein modification data comprises instructions to cause the dental replacement to scale in at least one of x-, y-, or z-direction relative to the bridge frame model.

23. The method of claim 19, wherein modification data comprises instructions to cause the coping layer's exterior surface to scale in one of the x-, y-, or z-directions, relative to the scanned adjacent tooth.

24. The method of claim 14, wherein calculating the third three-dimensional image data includes using data from a library of bridge units.

25. The method of claim 24, wherein calculating third three-dimensional image data further comprising to determining and positioning connections between bridge units.

26. The method of claim 14, further comprising determining and positioning, in the virtual three-dimensional model, holding pins for holding the milled dental replacement in a material blank.

27. The method of claim 14, wherein modification data is received from a keyboard and/or pointing device.

* * * * *

UNITED STATES PATENT AND TRADEMARK OFFICE
CERTIFICATE OF CORRECTION

PATENT NO.        : 7,695,281 B2                                             Page 1 of 1
APPLICATION NO.   : 10/987492
DATED             : April 13, 2010
INVENTOR(S)       : Bernd Burger It is certified that error appears in the above-identified patent and that said Letters Patent is hereby corrected as shown below:

Title Page
Item [73] Assignee:
    Delete "3M Innovative Properties Company, St. Paul, Minnesota" and
    insert -- 3M ESPE AG, Seefeld, Germany -- therefor.

Column 10
Line 30, Claim 18, delete "situation or the" and
        insert -- situation of the -- therefor.

Signed and Sealed this
Thirteenth Day of December, 2011

David J. Kappos
*Director of the United States Patent and Trademark Office*